United States Patent [19]

Day

[11] Patent Number: 6,040,315
[45] Date of Patent: Mar. 21, 2000

[54] ANTACID CO-POLYMER OF GUANIDINE AND POLYETHYLENIMINE

[76] Inventor: Charles E. Day, 1434 Sunbeam Rd., Leitchfield, Ky. 42754

[21] Appl. No.: 09/182,116

[22] Filed: Oct. 29, 1998

Related U.S. Application Data

[60] Provisional application No. 60/064,419, Oct. 30, 1997.

[51] Int. Cl.$^7$ ...................................................... A01N 43/42
[52] U.S. Cl. ........................ 514/310; 514/255; 514/275; 544/320; 544/321
[58] Field of Search ..................................... 514/310, 275, 514/255; 544/320, 321

[56] References Cited

U.S. PATENT DOCUMENTS

| | | | |
|---|---|---|---|
| 5,607,936 | 3/1997 | Chaing et al. | 514/255 |
| 5,863,924 | 1/1999 | Berger et al. | 514/275 |

*Primary Examiner*—Terressa M. Boykin

[57] ABSTRACT

Herein is disclosed how to make and to use a nonmetallic antacid composition which is the product of the co-polymerization of guanidine and polyethylenimine. The resultant polymer is useful as an antacid.

3 Claims, No Drawings

ANTACID CO-POLYMER OF GUANIDINE AND POLYETHYLENIMINE

CROSS-REFERENCE TO RELATED APPLICATIONS

This application incorporates by reference the applicant's U.S. Provisional Application No. 60/064,419, filed Oct. 30 1997, from which priority is claimed.

DRAWINGS

Not Applicable.

SEQUENCE LISTING

Not Applicable.

STATEMENT REGARDING FEDERALLY SPONSORED RESEARCH

Not Applicable.

REFERENCE TO A "MICROFICHE APPENDIX"

Not Applicable.

FIELD OF THE INVENTION

The invention relates to a composition useful as an antacid.

DESCRIPTION OF THE RELATED ART

Antacid compositions known in the art include a multitude based on a few ionic compounds, predominantly salts of magnesium, aluminum or bismuth. For example, U.S. Pat. No. 4,425,332 discloses a dosage form of finely divided aluminum hydroxide. More recently, U.S. Pat. No. 5,762,962 discloses compositions based on calcium or magnesium salts. These are representative of the art, which continues to rely heavily, indeed almost exclusively, on the use of a few metal salts. In addition, some citrates, tartrates and silicates are used as antacids, as are milk solids and even the amino acid glycine. Regulations concerning over-the-counter antacid use are found in 21 CFR 331, which is incorporated by reference.

A major problem associated with the use of metallic antacids is their well-documented adverse interaction with widely-used drugs, including especially tetracycline and quinolone antibiotics, whose absorption is inhibited by the same cations present in widely-used antacids. Adverse interactions between antacids and various drugs are discussed in: Marchbanks C R (1993) Drug-drug interactions with fluoroquinolones. *Pharmacotherapy* 13, 23S; Gugler R & Allgayer H (1990) Effects of antacids on the clinical pharmacokinetics of drugs. *Clin Pharmacokinet* 18, 210; Bint A J & Burtt I (1980) Adverse antibiotic drug interactions. *Drugs* 20, 57. Moreover, many metallic antacids are not suitable for use by patients who present with kidney disease. Hatlebakk J G & Berstad A (1996) Pharmacokinetic optimisation in the treatment of gastro-oesophageal reflux disease. *Clin Pharmacokinet* 31, 386.

For treatment of underlying causes of the discomfort traditionally relieved by antacids, a number of small molecule pharmaceutical compositions have been developed. The best-known and most widely prescribed of such medications include the H-2 histamine receptor antagonists (e.g., U.S. Pat. No. 4,496,571) and the proton pump inhibitors (e.g., U.S. Pat. No. 5,677,302). The mechanism of action of such agents inheres in their small molecule structure, evidently capable of binding to cellular receptors. The use and mechanism of such agents is discussed in: Hirschowitz B I et al. (1995) Pharmacological aspects of acid secretion. *Dig Dis Sci* 40, 3S.

While an effective therapy for many individuals, small molecule drugs for the treatment of hypersecretory conditions are not without side-effects. Hatlebakk J G & Berstad A (1996) Pharmacokinetic optimisation in the treatment of gastro-oesophageal reflux disease. *Clin Pharmacokinet* 31, 386.

There has therefore been a need for a non-metallic, polymeric antacid.

No co-polymer of guanidine and polyethylenimine such as that disclosed herein has been known in the art.

Moreover, no co-polymer of guanidine is known in the art as an antacid. Small molecule agents, such as guanidinothiazoles, which are not polymers, have been included in disclosed antacid preparations, as in U.S. Pat. No. 5,817,340. It should be emphasized that guanidinothiazoles are structurally distinct from guanidine, and that such agents are small molecule drugs, whereas the instant invention is a macromolecular polymer.

Furthermore, no co-polymer of polyethylenimine is known in the art as an antacid. Fluorinated polymers, one embodiment of which includes guanidineformaldehyde polycondensate, have been disclosed in U.S. Pat. No. 4,536,298 for use as fire extinguishers. Again, such fluorinated polymers are structurally distinct from the instant invention, which is a co-polymer of underivatized guanidine and polyethylenimine.

BRIEF SUMMARY OF THE INVENTION

Herein I describe how to make and use a nonmetallic antacid composition, which is the product of the co-polymerization of guanidine and polyethylenimine. The resultant polymer possesses significant acid-binding capacity.

The invention thus satisfies a need for a non-metallic antacid.

As a treated polymer, the invention herein disclosed does not rely on binding to cellular receptors as do small molecule drugs. Therefore the absorption into the bloodstream and consequent biotransformation which are attendant to the effective use of many small molecule drugs are not required for the use of the invention herein disclosed. Instead, as an acid-neutralizing polymer, the instant invention inherently possesses its antacid property: there is no need for the polymer to be absorbed from the lumen of the alimentary canal in order for it to exert its antacid effect.

The fact that no co-polymer of guanidine and polyethylenimine such as that disclosed herein is known in the art, given the ready availability of these two starting materials, lends support to the conclusion that the art in effect teaches away from the notion that such a co-polymer can be formed between the two.

BRIEF SUMMARY OF THE SEVERAL VIEWS OF THE DRAWING

Not Applicable.

DETAILED DESCRIPTION OF THE INVENTION

A quantity of 500 mg of guanidine carbonate was weighed into a 13×100 mm glass culture tube. A volume of 1 mL of distilled water was added and the contents of the tube were mixed. Concentrated $H_2SO_4$ was added dropwise until foaming stopped, and then one extra drop was added. A quantity of 800 mg of 50% polyethylenimine (PEI; Polymin P) was added and the contents of the tube were mixed and heated to about 90° C. After cooling the tube to where it was just warm to the touch, a volume of 0.5 mL of 38% HCHO was added dropwise. The tube contents polymerized almost immediately. The polymer was broken up with a metal spatula. A volume of 5 mL of acetone was added and the polymer was thoroughly broken up with a metal spatula. The tube, including contents, was centrifuged 1 min at 2000 rpm. The acetone supernatant was discarded. The polymer was washed twice more with 5 mL acetone. Next, the precipitate was suspended in acetone, and the suspension was then filtered on Whatman #1 filter paper. The polymer retained on the filter paper was blotted on an absorbent paper towel, air-dried for 1 h at room temperature, transferred to a glass vial and weighed.

On a larger scale, a quantity of 10 g of guanidine carbonate was weighed into a 250 mL glass beaker. A volume of 20 mL distilled water was added and the beaker was placed on a magnetic stirrer for the guanidine carbonate to dissolve. Concentrated $H_2SO_4$ was added dropwise with stirring until no more fizzing occurred, after which a few extra drops of concentrated $H_2SO_4$ were added. Next, a quantity of 16 g of polyethylenimine, 50% solution in water was added and the beaker was placed on a stirrer to mix the contents thoroughly. After the mixing, the beaker was placed on a hot plate on low heat and heated to 90° C. The beaker was then placed on a magnetic stirrer and the contents were allowed to cool to 50° C. whereupon a volume of 10 mL of 38% formaldehyde was added with stirring. The contents of the beaker gelled almost immediately. The gel was broken up finely and mixed with a metal spatula until it had cooled to room temperature. A volume of 50 mL of acetone was added to the beaker and the contents were mixed with a metal spatula. The polymer was allowed to settle and the acetone was poured off and discarded. The polymer was washed twice more with 50-mL portions of acetone. After the last acetone wash the polymer was removed from the beaker and drained thoroughly on absorbent paper towels and allowed to air-dry at room temperature for about 30 min.

In order to prepare this polymer for use as an agent for the neutralization of acid, the dried polymer was then placed in a beaker and a volume of 200 mL of 1 M NaOH was added. The contents were mixed with a metal spatula and allowed to stand at room temperature for 30 min. The supernatant NaOH was decanted and a further volume of 200 mL of NaOH was added, mixed with the polymer, and allowed to stand at room temperature for 30 min. The supernatant NaOH was decanted and the beaker was filled with about 150 mL distilled water, which was mixed with the polymer. After the polymer settled, the distilled water supernatant was decanted and discarded. The polymer was washed with distilled water four more times in this manner. After the last distilled water wash, the polymer was transferred to Whatman #1 filter paper on top of absorbent paper towels and allowed to drain thoroughly. After draining, the polymer was placed in an incubator at 40° C. for 3 h to dry. The dried polymer was transferred to a Tekmar analytical mill and milled for 2 min.

The polymer possessed significant acid-binding capacity. A quantity of 100 mg of the polymer was added to a glass 25 mL Erlenmeyer flask containing 5 mL distilled water. To the flask was added 6.5 mL of 0.10 N HCl. The flask was placed on a magnetic stirrer for one hour at room temperature, whereupon the pH was measured and found to be 4.0.

Hence the polymer is useful as an antacid.

As an example, the polymer, in a formulation comprising the polymer and any needed binders or excipients, is useful as a pharmaceutical for the neutralization of hydrochloric acid in a human patient in need of such treatment.

As another example, the polymer is administered to a human patient in need of treatment for relief of duodenal ulcer, gastric ulcer, gastroesophageal reflux disease, esophagitis, or pathological hypersecretory condition.

As yet another example, the polymer is useful for formulation in a multi-mechanism antacid comprising the polymer and any agent chosen from the group consisting of the $H_2$ histamine receptor antagonists and the proton pump inhibitors. While I do not wish to be bound by theory, it appears that the polymer acts in the lumen of the alimentary canal, binding hydrogen ions, while the $H_2$ antagonist or proton pump inhibitor acts at the surface of epithelial cells to prevent further secretion of acid.

As still another example, an agent comprising the polymer and any of the group consisting of ranitidine, famotidine, nizatidine, cimetidine, omeprazole, and lansoprazole is administered to a human patient in need of treatment for relief of duodenal ulcer, gastric ulcer, gastroesophageal reflux disease, esophagitis, or pathological hypersecretory condition.

As a further example, an agent comprising from about 0.5 to about 10 g of the polymer and any of the group consisting of from about 50 mg to about 300 mg ranitidine, from about 10 mg to about 40 mg famotidine, from about 75 mg to about 300 mg nizatidine, from about 400 mg to about 2400 mg cimetidine, from about 10 mg to about 50 mg omeprazole, and from about 10 mg to about 120 mg lansoprazole is administered to a human patient in need of treatment for relief of duodenal ulcer, gastric ulcer, gastroesophageal reflux disease, esophagitis, or pathological hypersecretory condition.

As another example, an agent comprising the polymer and any of the group consisting of the nonsteroidal anti-inflammatory drugs is administered for the prevention or treatment of inflammation in a human patient for whom it is desired to minimize gastrointestinal complications of treatment with said nonsteroidal anti-inflammatory drug.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can legally be accorded to the appended claims.

I claim:

1. A composition of matter which is a co-polymer of guanidine carbonate and polyethylenimine, wherein the mass ratio of guanidine carbonate to polyethylenimine is about 5:4.

2. A composition resulting from a process comprising the steps of:

(a) dissolving guanidine carbonate in water to form an initial solution;

(b) adding $H_2SO_4$ to the initial solution to form an acidified solution;

(c) adding polyethylenimine to the acidified solution to form an intermediate mixture;

(d) heating the intermediate mixture to form a heated mixture;

(e) cooling the heated mixture to form a penultimate mixture; and (f) adding formaldehyde to the penultimate mixture.

3. A composition resulting from a process comprising the steps of:

(a) dissolving about 5 parts guanidine carbonate, by mass, in water to form an initial solution;

(b) adding $H_2SO_4$ to the initial solution to form an acidified solution;

(c) adding about 4 parts polyethylenimine, by mass, to the acidified solution to form an intermediate mixture;

(d) heating the intermediate mixture to form a heated mixture;

(e) cooling the heated mixture to form a penultimate mixture; and (f) adding about 2 parts formaldehyde, by mass, to the penultimate mixture.

* * * * *